US011083911B2

(12) United States Patent
Joe Anto et al.

(10) Patent No.: US 11,083,911 B2
(45) Date of Patent: Aug. 10, 2021

(54) RADIATION THERAPY INTERACTIVE PLANNING

(71) Applicant: KONINKLIJKE PHILIPS N.V., Eindhoven (NL)

(72) Inventors: Gipson Joe Anto, Kaliyal (IN); Sivaramakrishnan Krishnaiyer Raman, Bangalore (IN); Vaitheeswaran Ranganathan, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 185 days.

(21) Appl. No.: 16/083,596

(22) PCT Filed: Apr. 1, 2017

(86) PCT No.: PCT/EP2017/057793
§ 371 (c)(1),
(2) Date: Sep. 10, 2018

(87) PCT Pub. No.: WO2017/178257
PCT Pub. Date: Oct. 19, 2017

(65) Prior Publication Data
US 2019/0070435 A1    Mar. 7, 2019

Related U.S. Application Data

(60) Provisional application No. 62/321,896, filed on Apr. 13, 2016.

(51) Int. Cl.
*A61N 5/10*    (2006.01)

(52) U.S. Cl.
CPC .......... *A61N 5/1031* (2013.01); *A61N 5/103* (2013.01); *A61N 5/1039* (2013.01); *A61N 5/1048* (2013.01); *A61N 2005/1074* (2013.01)

(58) Field of Classification Search
None
See application file for complete search history.

(56) References Cited

U.S. PATENT DOCUMENTS

| 6,360,116 B1 | 3/2002 | Jackson |
| 2005/0111621 A1 | 5/2005 | Riker |

(Continued)

FOREIGN PATENT DOCUMENTS

| EP | 2260902 | 12/2010 |
| JP | 2002263208 A | 9/2002 |

(Continued)

*Primary Examiner* — Hoon K Song

(57) ABSTRACT

A radiation therapy system (100) includes a radiation therapy (RT) optimizer unit (102) and an interactive planning interface unit (120). The RT optimizer unit (102) receives at least one target structure and at least one organ-at-risk (OAR) structure segmented from a volumetric image (108), and generates an optimized RT plan (140) based on dose objectives (200-204, 210-222, 320), at least one dose objective of the dose objectives corresponding to each of the at least one target structure (210-222) and the at least one OAR structure (200-204). The optimized RT plan includes a planned radiation dose for each voxel of the volumetric image using external beam radiation therapy, wherein the RT optimizer unit operates iteratively. The interactive planning interface unit (120) interactively controls each of the dose objectives through controls (300) displayed on a single display (126) of a display device (124), operates the RT optimizer unit to iteratively compute the planned radiation dose according to the controls, and provide visual feedback (310, 134) on the single display according to progress of the RT optimizer unit after each trial.

20 Claims, 5 Drawing Sheets

(56) References Cited

U.S. PATENT DOCUMENTS

| | | |
|---|---|---|
| 2007/0201614 A1 | 8/2007 | Goldman |
| 2008/0081991 A1 | 4/2008 | West |
| 2012/0157746 A1* | 6/2012 | Meltsner ................ G16H 50/50 600/1 |

FOREIGN PATENT DOCUMENTS

| | | |
|---|---|---|
| WO | 2005/035061 | 4/2005 |
| WO | 2011024085 | 3/2011 |
| WO | 2016198979 | 12/2016 |

* cited by examiner

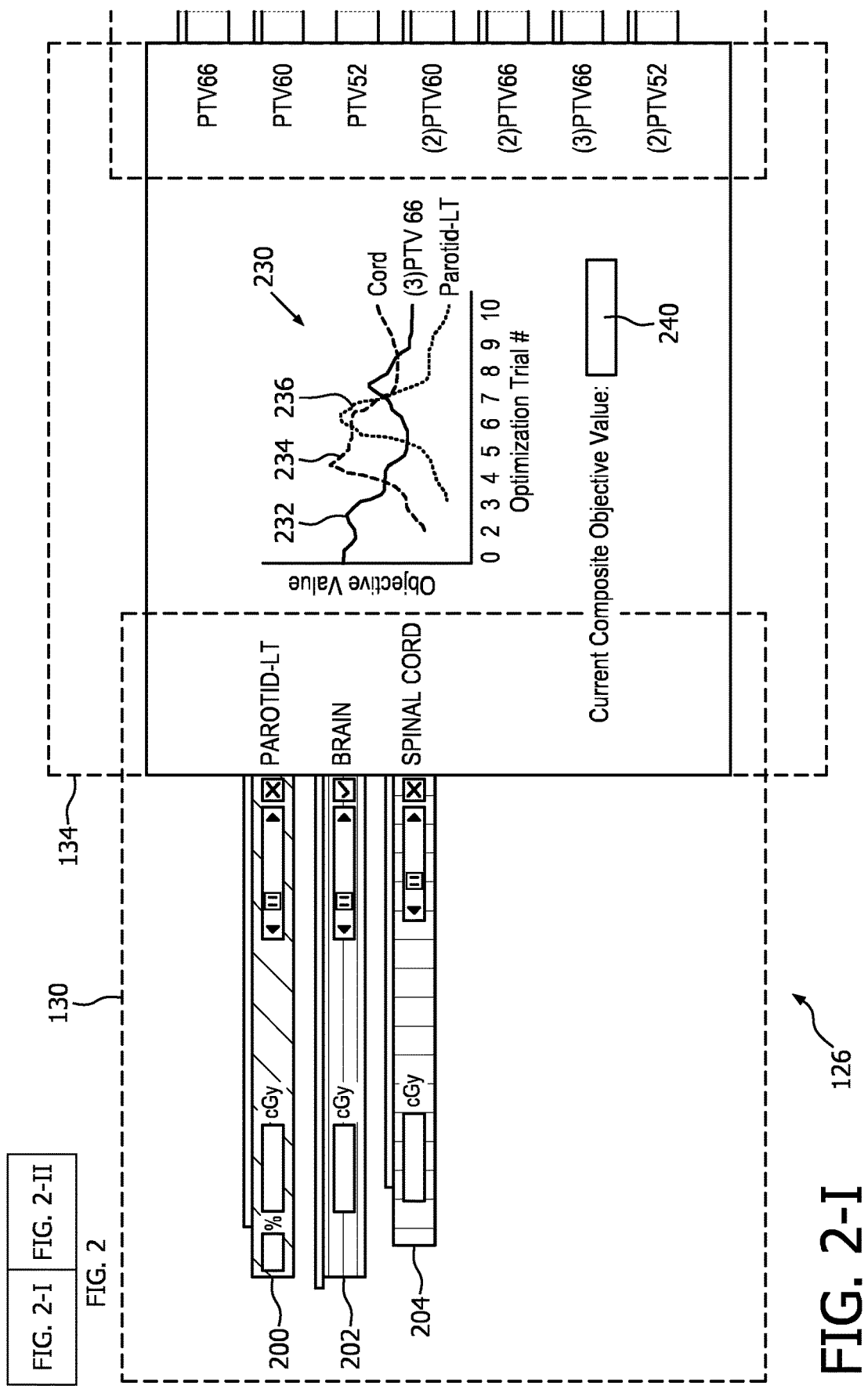
FIG. 2-I

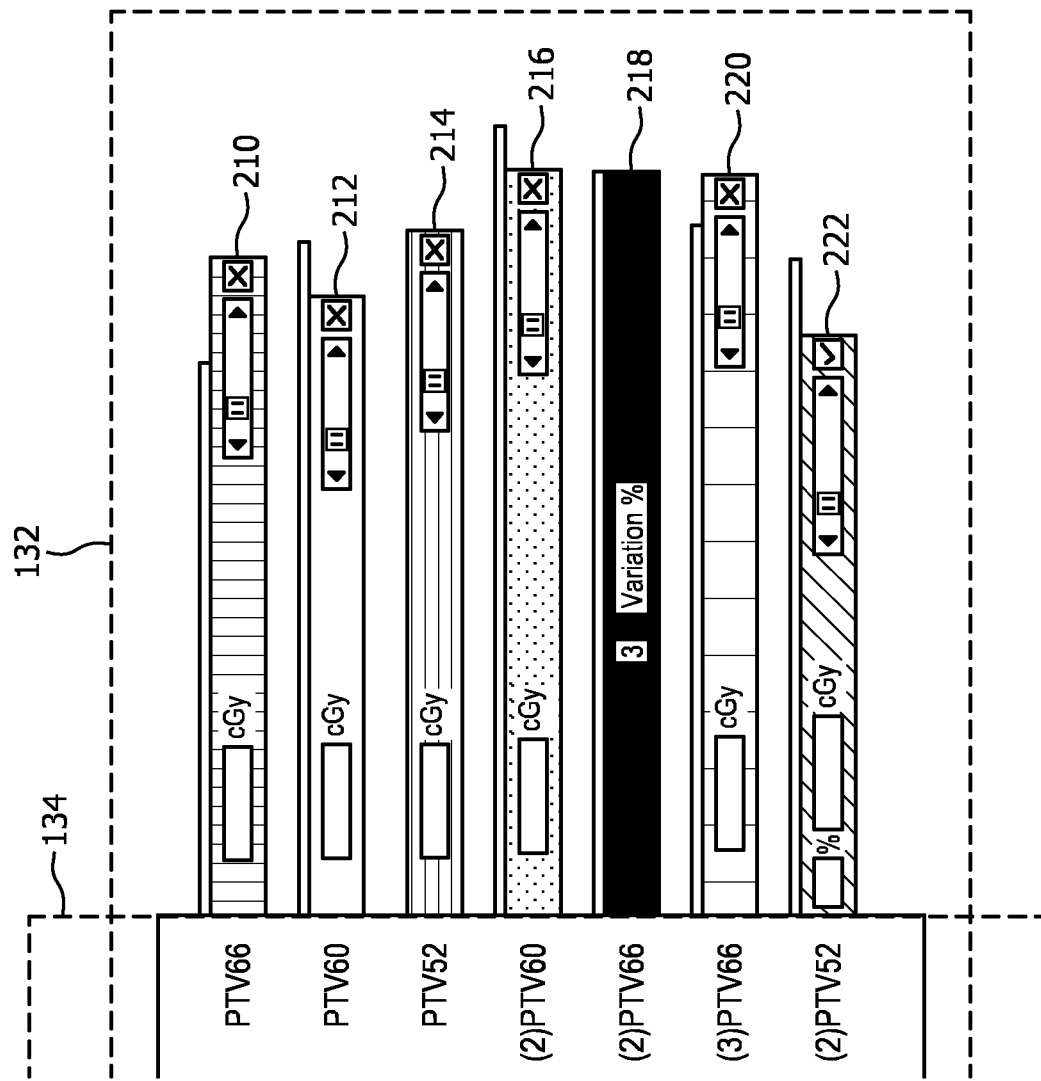
FIG. 2-II

RADIATION THERAPY INTERACTIVE PLANNING

CROSS REFERENCE TO RELATED APPLICATIONS

This application is the U.S. National Phase application under 35 U.S.C. § 371 of International Application No. PCT/EP2017/057793 filed Apr. 1, 2017, published as WO 2017/178257 on Oct. 19, 2017, which claims the benefit of U.S. Provisional Patent Application No. 62/321,896 filed Apr. 13, 2016. These applications are hereby incorporated by reference herein.

FIELD OF THE INVENTION

The following generally relates to external beam radiation therapy, and is described with particular application to inverse planning optimization techniques, such as Intensity Modulate Radiation Therapy (IMRT), Intensity Modulated Proton Therapy (IMPT) and/or Volumetric Modulated Arc Therapy (VMAT) radiation therapy planning.

BACKGROUND OF THE INVENTION

IMRT, IMPT and/or VMAT radiation therapy techniques deliver high doses to target areas, such as cancerous growth, to destroy or control diseased tissues in the target area. Dose goals are identified by a healthcare practitioner based on one or more volumetric planning images, e.g. an X-ray Computed Tomography (CT) image. Based on the dose goals an optimizer is used to plan the orientation, duration, shape and/or intensity of beams of external radiation to the target areas. The inversely planned external beams according to dose objectives is different from other radiation therapy direct planning methods, such as brachytherapy, where a point source and location is specified and the dose is computed from the point source and location. In inverse planning methods, target volumes and nearby organs or organs-at-risk (OARs) are identified in the planning images and are typically segmented as structures, e.g. sub-volumes from the planning image.

In delivering the beams of external radiation, which pass through the body from a radiation source, organs in the path of the radiation beams are also subject to the delivered radiation. Organs can be classified as serial organs or parallel organs. Serial organs, such as a brain stem, spinal cord, etc., which receive lethal doses of radiation to any one part of the serial organ causes the entire organ to fail. Parallel organs, such as a parotid gland, larynx, lips, etc. can receive lethal doses to a portion of the parallel organ and still maintain at least some function from the remaining portions.

Planning methods for the beams of external radiation typically include competing objectives. Some objectives call for delivering radiation to target volumes. Other objectives call for not delivering radiation or only permitting delivery of a certain amount to the OARs. OAR objectives typically include a maximum dose goal or maximum dose volume histogram (DVH), and a weight or priority of the objective relative to other OAR objectives. Target objectives typically include a minimum radiation dose goal or uniform dose goal. An optimizer program inputs the target and OAR objectives and volumes with the dose goals, and identifies a set of beams, each of an intensity, duration, shape and orientation, which optimally meet the competing objectives to form a plan. The weights correspond to segmented volumes, such as the OARs and target volumes, for which a planned dose is computed using weight applied to the entire segmented volume based on the weighted objective.

A healthcare practitioner reviews the output from the optimizer typically viewed as planned or expected doses expressed volumetrically, such as iso-contours imposed on the planning image, dose volume histograms, and the like. In a review process, objectives can be changed, e.g. change a weight or a dose goal, or objectives can be added. The added objectives can direct the dose, such as more to certain target areas or less to certain OARs. The added objectives can include subsets of the segmented structures or additional structures with corresponding dose goals to alter or shift planned doses. The optimizer program is re-run with the changed/additional objectives, and the process repeated until an acceptable optimized plan is reached.

However, planning is a complex and time consuming task especially for IMRT Simultaneous Integrated Boost cases. Adding objectives in the inverse planning optimization can add interactions with other objectives, which can cause contradictions in the optimization process. An optimizer in inverse planning may not converge and a nature of which objectives are contradictory may not be readily apparent. For example, a spatial position and dose objectives of one segmented structure with external beams of radiation may be in opposition to dose objectives of another segmented structure. Moreover, progress of the optimizer toward an acceptable solution can be difficult to ascertain. A healthcare practitioner can spend a great deal of time trying different combinations of objectives and weights for a planning image in order to discover any contradictions between objectives as well as trying to identify whether the optimization process is improving or cycling, e.g. not converging.

With different dose objectives according to target and OAR structures and parameters for each, set-up and control of the optimizer alone becomes a complex task. Keeping track of the different dose objectives and parameters typically involve either command line entry or a series of screens, which are typically separated from the output of the optimizer.

Additionally, some approaches to provide information to the healthcare practitioner reviewing progress of the plan use a spatial view of the doses shown using iso-contours, which provide a visualization of doses superimposed on the planning image. However, the iso-contours make it difficult to understand and identify overall progress and contradictions interpreted throughout the iso-contours over an entire planning volume that the healthcare practitioner must navigate. In addition, it is difficult to compare development of a previously optimized plan that has similarities with a current plan to aid in deciding or initializing optimization parameters.

SUMMARY OF THE INVENTION

Aspects described herein address the above-referenced problems and others.

The following describes a radiation therapy (RT) system with an interactive control of a RT optimizer unit, and visual feedback on progress of each dose objective and overall progress toward an acceptable optimized RT plan. The control and visual feedback can be concurrent with the operation of the RT optimizer unit.

In one aspect, a radiation therapy system includes a radiation therapy (RT) optimizer unit and an interactive planning interface unit. The RT optimizer unit receives at least one target structure and at least one organ-at-risk (OAR) structure segmented from a volumetric image, and generates an optimized RT plan based on dose objectives, at least one dose objective of the dose objectives corresponding to each of the at least one target structure and the at least one OAR structure. The optimized RT plan includes a planned radiation dose for each voxel of the volumetric image using external beam radiation therapy, wherein the RT optimizer unit operates iteratively. The interactive planning interface unit interactively controls each of the dose objectives through controls displayed on a single display of a display device, operates the RT optimizer unit to iteratively compute the planned radiation dose according to the controls, and provide visual feedback on the single display according to progress of the RT optimizer unit after each trial.

In another aspect, a method of radiation therapy includes interactively controlling each of a plurality of dose objectives through controls displayed on a single display of a display device, wherein the plurality of dose objectives corresponding to at least one target structure and at least one organ-at-risk (OAR) structure segmented from a volumetric image, at least one dose objective of the plurality of dose objectives corresponding to each of the at least one target structure and the at least one OAR structure. The optimized RT plan includes a planned radiation dose for each voxel of the volumetric image using external beam radiation therapy. An optimized RT plan is iteratively computed by an RT optimizer unit according to the controls. Visual feedback is provided on the single display according to progress of the RT optimizer unit after each trial.

In another aspect, a radiation therapy system includes a non-transitory storage medium configured with program instructions and a therapy control device. The program instructions when executed by one or more processors interactively control each of a plurality of dose objectives through controls displayed on a single display of a display device, wherein the plurality of dose objectives correspond to at least one target structure and at least one organ-at-risk (OAR) structure segmented from a volumetric image, at least one dose objective of the plurality of dose objectives correspond to each of the at least one target structure and the at least one OAR structure. The optimized RT plan includes a planned radiation dose for each voxel of the volumetric image using external beam radiation therapy. The program instructions when executed by the one or more processors iteratively compute an optimized RT plan by an RT optimizer unit according to the controls. The program instructions when executed by the one or more processors provide visual feedback on the single display according to progress of the RT optimizer unit after each trial. The therapy control device generates control instructions for a radiation delivery device to deliver radiation according to the optimized RT plan.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIG. 2 illustrates an exemplary RT system interactive planning interface with control of the RT optimizer unit and visual feedback.

DETAILED DESCRIPTION OF EMBODIMENTS

Figure 1:
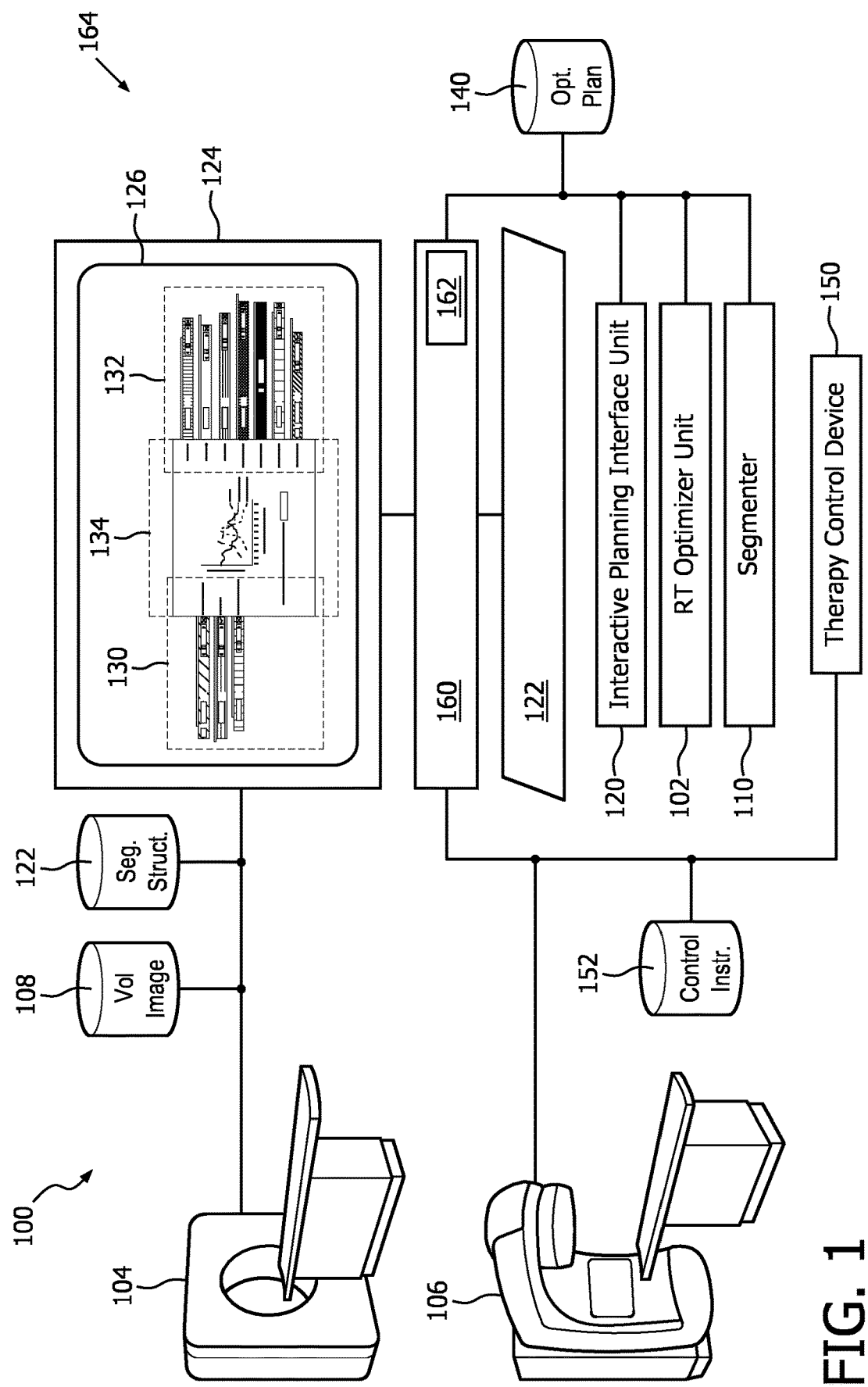
FIG. 1 schematically illustrates an embodiment of a RT system with interactive control of a RT optimizer unit and visual feedback.

Initially referring to FIG. 1, an example RT system 100 with interactive control of an optimizer unit 102 in connection with an imaging device 104 and a radiation delivery device 106 is schematically illustrated. The imaging device 104 includes a scanner of one or more modalities such as an X-ray Computed Tomography (CT) scanner, Magnetic Resonance Imaging (MRI) scanner, a Positron Emission Tomography (PET) scanner, a Single Proton Emission Computed Tomography (SPECT) scanner, combinations, hybrids and the like, which generates a volumetric image 108 of a region of interest (ROI) of a subject used to plan the radiation therapy. The volumetric planning image 108 includes at least a three-dimensional (3D) image, e.g. volume image constructed from 2D slices, 3D image, 4D image, etc. The volumetric planning image 108 can be received directly from the imaging device 104 or stored in an electronic memory, such as a Picture Archiving and Communication System (PACS), a Radiology Information System (RIS), an Electronic Medical Record (EMR), cloud storage, server storage, local storage, and the like.

A segmenter 110 identifies and segments structures 112 from the volumetric planning image 108. The segmenter 110 identifies and segments the structures 112 automatically or manually using known or other segmentation techniques. The segmented structures 112 include one or more target structures, such as tumors, diseased tissue, and the like. The segmented structures 112 include one or more OAR structures. The OAR structures include serial and/or parallel organs. Each segmented structure 112 is a volumetric structure and can be defined spatially by a subset of voxels in the volumetric planning image 108. A voxel can be included in more than one segmented structure. For example a target structure can overlap with an OAR structure, such as a portion of the OAR including diseased tissue.

An interactive planning interface unit 120 interactively controls the RT optimizer unit 102 with controls displayed on an interactive planning interface 126 in a single display on a display device 124 and provides visual feedback through the interactive interface 126 single display. The controls operate with inputs from one or more input devices 122, such as a mouse, keyboard, microphone, touch screen, and the like. The interactive planning interface 126 provides interactive controls and feedback divided into three display regions. A first region 130 includes interactive controls and feedback for OAR dose objectives. A second region 132 includes interactive controls and feedback for target dose objectives. A third region 134 includes a measure of overall progress, e.g. a composite objective measure, and includes a graphical display of progress by the RT optimizer unit 102 over a number of trials. Each trial can include one or more iterations by the RT optimizer unit 102. A trial begins with each modification of dose objectives and ends with a result returned by the RT optimizer unit 102. The third region 134 can include general controls for the system. The first region 130 and the second region 132 are spatially separated on the single display. The three regions 130, 132 and 134 can include partial overlap.

In one embodiment the first region 130 and the second region 132 are located laterally to the third region 134. In one embodiment, the first region 130 and the second region 132 are located above and below the third region 134. Other arrangements are contemplated. The arrangement can vary according to the characteristics of the display device 124. In some instances, segregating and grouping the OAR dose objectives in a first region 130 separated from the segregated and grouped target dose objectives in the second region 132 allows easier visual monitoring and comprehension by the healthcare practitioner for a potential contradiction. For example, with a changed dose goal in a first OAR dose objective, feedback on progress other dose objectives can be easily monitored for a decline or adverse impact. In some instances, the third region 134 can provide a graphical indication of a contradiction with a change/addition in an objective. The graphical indication can include sharp changes in plotted direction of objective values, local maxima or minima of objective values, cycling of plotted objective values between the added/changed objective and another objective, plotted objectives values sloped away from satisfied objectives, and the like. In some instances, the graphical indications provide a visually concise view of a cause-effect of the added/change to objectives.

The interactive planning interface unit 120 operates the controls interactively while providing feedback concurrently or simultaneously. The controls allow a new dose objective or a change to an existing dose objective for a segmented structure 112 to be input. Each dose objective is a RT dose objective for a selected segmented structure 112, which is a target volume or an OAR. Each RT plan includes at least one objective controlled in the first region 130, which corresponds to a segmented structure 112 that is an OAR. Each RT plan includes at least one objective controlled in the second region 132, which corresponds to a segmented structure 112 that is a target volume. Each objective includes a corresponding volume, a type of dose objective, and one or more dose parameters. Dose parameters can include a weight, a percentage variation, and/or a hard constraint indicator.

The RT optimizer unit 102 receives the parameters for each of the dose objectives specified by the controls and iteratively generates an optimized plan 140 using an inverse planning algorithm known in the industry. An example of an iterative RT inverse planning algorithm can be found in U.S. patent application "Radiation Therapy Optimization Unit with Global Considerations" filed Jun. 9, 2015 Ser. No. 62/172,267. With each trial of the RT optimizer unit 102, the interactive planning interface unit 120 provides feedback on progress of each objective and on overall progress according to values returned, e.g. the changed optimized plan 140 by the RT optimizer unit between changes to the dose objectives. With each iteration of the RT optimizer unit 102, the interactive planning interface unit 120 can provide feedback on progress of each objective and on overall progress according to values returned at each iteration, e.g. changes to the optimized plan 140 by the RT optimizer unit 102 by iteration. The feedback includes visual feedback. The RT optimizer unit 102 can includes the changes or additions to dose objectives at each iteration or trial. The displayed feedback can be reset or continued with each trial. The RT optimizer unit 102 can be stopped and started through inputs, such as function keys. The interactive planning interface 126 can include a status indicator which indicates the operational status of the RT optimizer unit 102, such as running, stopped, paused, current iteration identification, current trial identification and the like.

A therapy control device 150 receives the optimized plan 140 and generates a set of control instructions 152 for the radiation delivery device 106, such as a Linear Particle Accelerator (LINAC), a proton therapy device and the like, to deliver the beams of external radiation to the subject using IMRT, IMPT or VMAT.

The interactive planning interface unit 120, the segmenter 110, the RT optimizer unit 102, and the therapy control device 150 are suitably embodied by one or more configured data processors 160, such as a digital processor, a microprocessor, an electronic processor, an optical processor, a multi-processor, a distribution of processors including peer-to-peer or cooperatively operating processors, client-server arrangement of processors, and the like. The configured processor executes at least one computer readable instruction stored in computer readable storage medium ("memory") 162, which excludes transitory medium and includes physical memory and/or other non-transitory medium to perform the disclosed segmentation, optimization, feedback, optimizer control and control instruction generation techniques. The configured processor may also execute one or more computer readable instructions carried by a carrier wave, a signal or other transitory medium. The configured processor can comprise a computing device 164, such as a workstation, laptop, tablet, smart phone, body worn computing device, server, and the like. The computing device 164 can include the input device 122. The computing device 164 can include the display device 124. The lines between components represented in the exemplary diagram represent communications paths, which can be wired or wireless.

With reference to FIG. 2, an exemplary RT system interactive user interface 126 with control of the RT optimizer unit and visual feedback is illustrated. Co-located in the first region 130 are controls with feedback for OAR dose objectives. Each OAR dose objective includes co-located controls and visual feedback corresponding to the OAR dose objective. The co-located controls and visual feedback can be adjacent. In some instances, the co-located controls and visual feedback provide easier association for a healthcare practitioner in a cause-effect relationship. In some instances, the co-located OAR dose objectives provide easier reference and operation for the healthcare practitioner. The first region 130 shows example controls and feedback for a left parotid dose objective 200, controls and feedback for a brain dose objective 202, and controls and feedback for a spinal cord dose objective 204.

Co-located in the second region 132 are controls with feedback for target dose objectives. Each target dose objective includes co-located controls and visual feedback corresponding to the target objective. The second region 132 shows example co-located controls and visual feedback for a planned target volume PTV66 dose objective 210, a PTV60 dose objective 212, a PTV52 dose objective 214, a second PTV60 dose objective 216, a second PTV66 dose objective 218, a third PTV66 dose objective 220, and a second PTV52 dose objective 222. Multiple dose objectives can be used for a segmented structure 112, either an OAR or a target.

In the third region 134, a graph of objective values (vertical axis) versus trials (horizontal axis) 230 shows progress over a number of trials. The graph includes plotted objectives values for one or more objectives and/or composite objective values. The plotted objective values can be represented as line graphs, histogram, scatter plots, and the like. The plotted objective values can be plotted to be increasing or rising as objectives values are met, or the inverse. The graph 230 shows an example first line graph 232 corresponding to the PTV66(3) dose objective 220 present in the first trial of the RT optimizer unit 102. The graph 230 shows an example second line graph 234 corresponding to the spinal cord dose objective 204 that is added in the second trial of the RT optimizer unit 102. The graph 230 shows an example third line graph 236 corresponding to the left parotid dose objective 202 that is added in the third trial of the RT optimizer unit 102. The line graphs 232-236 are plotted with objective values decreasing as dose objectives are met, e.g. an objective value equal to zero means that the objective is completely met. The line graphs present in the graph 230 are selectable based on an input, such as a right mouse click on an objective and appropriate menu selection, right mouse click on the graph 230 and appropriate selection of the corresponding dose objective 200-204, 210-222.

The presence of a conflict can be seen in the line graph 234 corresponding to the spinal cord dose objective 204, which increases in objective values in trials 7-10. During the same trials, line graph 232 corresponding to PTV66(3) objective values and line graph 236 corresponding to the left parotid objective values decrease. Thus, a potential conflict exists in delivering dose to PTV66 between preserving the left parotid and the spinal cord. In response, the healthcare practitioner may choose to modify the left parotid dose objective 200 and/or the PTV66(3) dose objective 220 using the corresponding controls.

The graph 230 can be used for a trend analysis of the current plan. The interactive planning interface unit 120 can identify on the line graphs changes in objectives, which are displayed in text using a mouse pointer. For example, a mouse pointer selecting a trial number can display a text message, such as "Cord objective with a max dose of 45 Gy was added". Each trial can display the dose objectives and parameters for the corresponding trial. The interactive planning interface unit 120 can include one or more line graphs of other plans for comparison. For example, a line graph of a dose objective progress for similar plan can be included in the graph 230 and contrasted, such as a dotted line.

The third region 134 can include a current composite objective value 240, which provides an overall measure of progress in meeting all the objectives. The current composite objective value 240 can be represented as one of a range of values. The current composite objective value 240 is obtained from the RT optimizer unit 102. The values can be expressed as decreasing toward zero for dose objectives being met, or increasing for dose objectives being met, e.g. range of 0-100 where 100 means all objectives are met.

Figure 3:
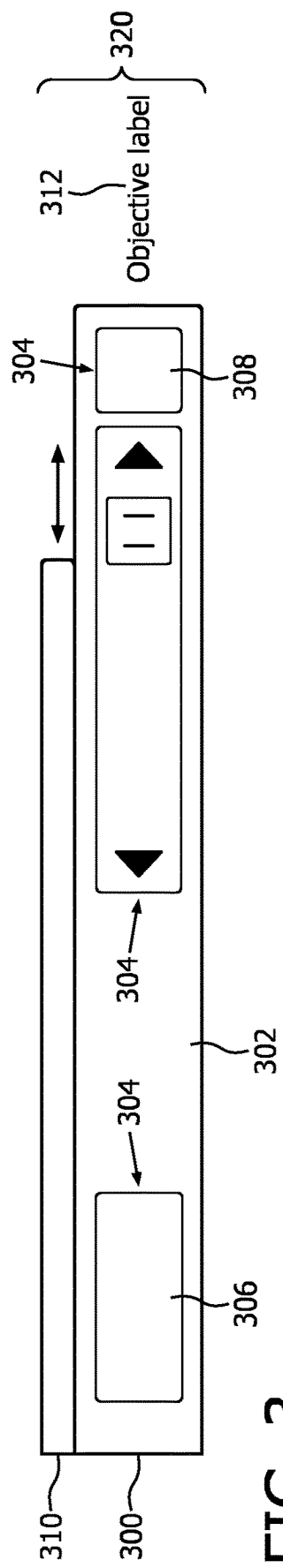
FIG. 3 illustrates an exemplary RT system interactive planning interface dose objective controls and dose feedback.

With reference to FIG. 3, an exemplary RT system user interface interactive controls 300 and feedback 310 for a dose objective 320 are illustrated. The dose objective 320 includes a label 322 or other indicator indicative of the corresponding segmented structure 112. The interactive controls 300 can be visualized in a rectangular area 302. The interactive controls 300 include a type of dose objective, which can be represented as a pattern and/or color of the rectangular area 302. For example, types of dose objectives can include 1) a maximum dose volume histogram or max DVH, 2) a minimum dose volume histogram or min DVH, 3) a maximum equivalent uniform dose or max EUD, 4) a minimum equivalent uniform dose or min EUD, 5) a maximum dose or max dose, 6) a minimum dose or min dose, 7) a uniform dose, 8) a target equivalent uniform dose or target EUD or 9) uniformity. Each type of dose objective can be represented different visually, such as in FIG. 2 with the left parotid dose objective 200 represented as max DVH with a first pattern, the brain dose objective 202 represented as max EUD with a second pattern, the spinal cord dose objective 204 and the PTV66(3) dose objective 220 represented as max dose with a third pattern, the PTV66 dose objective 210 represented as min dose with a fourth pattern, the PTV60 dose objective 212 represented as uniform dose with a fifth pattern, the PTV52 dose objective 214 represented as min EUD with a sixth pattern, the PTV60(2) dose objective represented as target EUD with a seventh pattern, the PTV66(2) dose objective represented as uniformity with an eighth pattern, and the PTV52(2) dose objective represented as min DVH with a ninth pattern. The dose objective type can be entered with an input from the input device 122, such as with a selection from a pop-up menu.

The objective control 300 includes one or more objective parameters 304. The input controls can be located within the rectangular area 302. In some instances, locating the input controls within the rectangular area 302 provides a fast association of the parameters with the corresponding dose objective. For example a radiation level 306 represented as an input box inputs the dose in units of cGy for the corresponding dose objective. An objective weight 308 can be represented as a slider bar. A hard constraint 308 can be represented as a check box. In one embodiment, the rectangular area 302 of the objective control 300 can be sized according to weight or priority relative to other objectives.

The objective feedback 310 includes an adjacent rectangular area or horizontal bar that provides feedback through color and/or size. The feedback represented includes a change from a previous trial or iteration. In one embodiment, the length of the horizontal bar is indicative of the percentage change from the prior trial. In one embodiment, the color of the horizontal bar represented as green or red indicates a positive or negative change respectively. In one embodiment, the horizontal bar indicates a measure of the current objective value.

Figure 4:
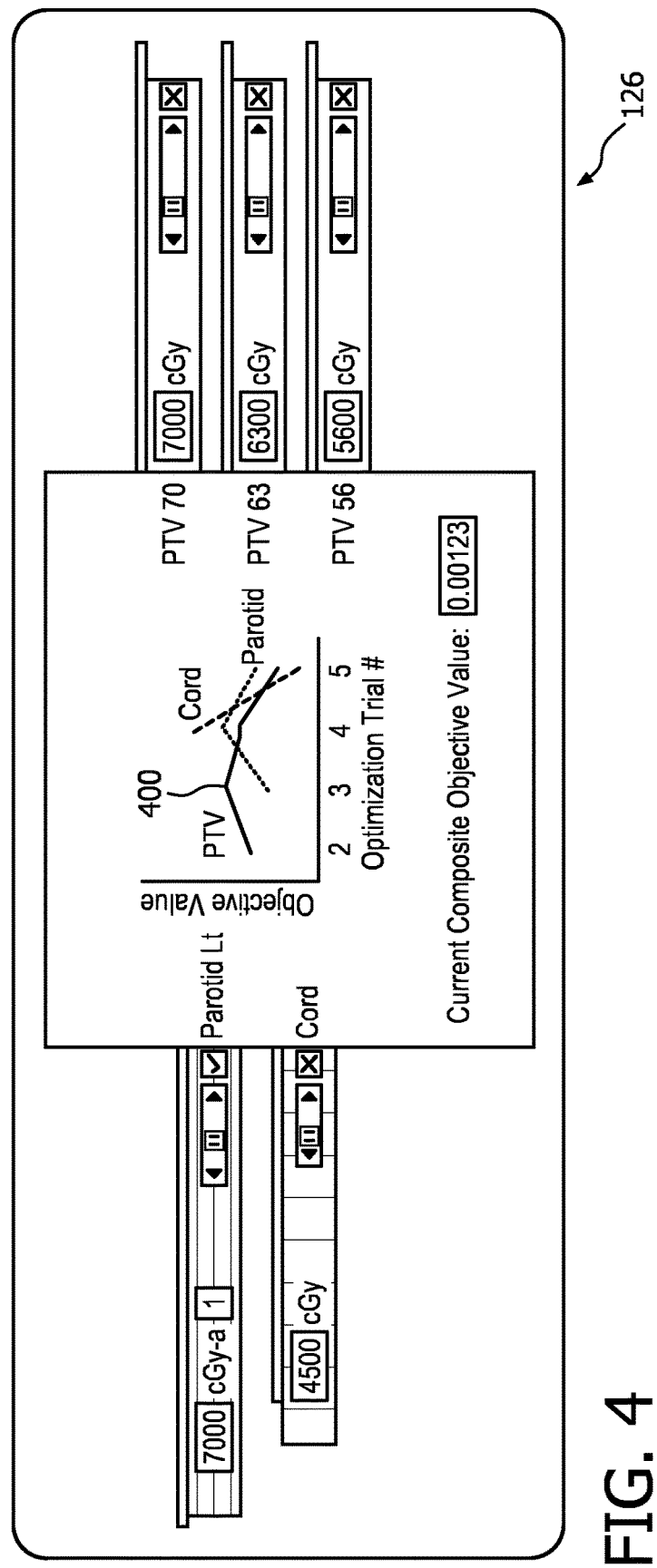
FIG. 4 illustrates another exemplary RT system interactive planning interface with control of the RT optimizer unit and visual feedback.

With reference to FIG. 4, another exemplary RT system interactive planning interface 126 with control of the RT optimizer unit and visual feedback is illustrated. The interactive planning interface 126 illustrates two OAR dose objectives, a left parotid dose objective and a spinal cord dose objective. The interactive planning interface 126 illustrates three target volume dose objectives, PTV70, PTV63, and PTV56. The RT optimizer unit 102 is started with the target dose objectives, and the left parotid dose objective added in the third trial, and the spinal cord dose objective added in the fourth trial. Different from FIG. 2, an increase in the weight of the left parotid dose objective avoids a conflict.

The graph of objective values versus trials (or iterations) 230 shows a composite line graph 400 for the target dose objectives. The graph visually illustrates a convergent and non-conflicting RT optimized plan for the different dose objectives. The line graphs are decreasing toward the axis indicative of the objectives being met. The current composite objective value is 0.00123, which close to zero indicative of all objectives being met. The individual dose objectives show feedback bar lengths indicative of each objective being met, except for the spinal cord dose objective. Further trials may yield an acceptable solution for the spinal cord dose objective.

Figure 5:
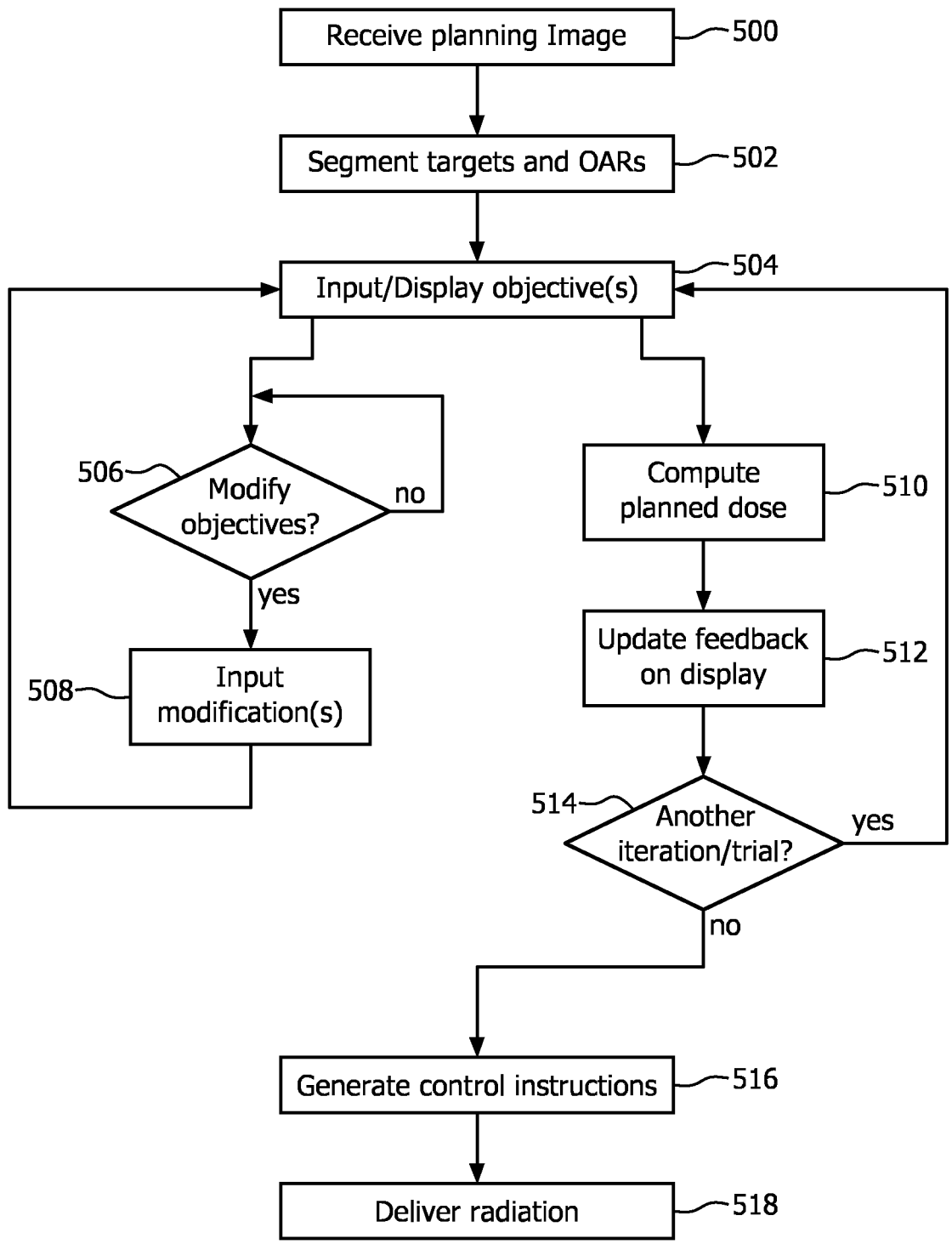
FIG. 5 flowcharts an embodiment of a method for RT planning with the interactive control of the RT optimizer unit and visual feedback.

With reference to FIG. 5, an embodiment of a method for RT planning with the interactive control of the RT optimizer unit and visual feedback is flowcharted. At 500, the volumetric image 108 is received. The volumetric image 108 can be received from electronic memory or directing from the imaging device 104.

At 502, the OAR and target segmented structures 112 are segmented from the volumetric image 108. At least one OAR and at least one target are segmented.

At 504, the controls (300) interactively specify each dose objective, control the RT optimizer unit 102, and provide feedback through a single display. The dose objectives include at least one dose objective 320 for at least one OAR segmented structure in the first region 130 of the single display. The dose objectives include at least one dose objective 320 for at least one target segmented structure in the second region 132 of the single display. The feedback includes the feedback 310 for each dose objective. The feedback includes the graph 230 in the third region 134, which graphically illustrates progress of the RT optimizer unit 102 according to the trials.

An input from an input device 122 indicates a modification to the dose objectives at 506. The modification can include a change to one or more parameters of one or more dose objectives. The modification can include a new dose objective. The new dose objective can be for an added segmented structure, OAR or target. The new dose objective can be an additional dose objective for a present segmented structure, OAR or target, e.g. a second dose objective for a same structure. Acts 504 and 506 can operate cyclically to interactively control the dose objectives.

At 510, the RT optimizer unit 102 computes a planned dose based on the objective controls, i.e. the current dose objectives and parameters. The RT optimizer unit 102 returns objective values for each objective and the current composite objective value. At each trial or iteration the current optimized plan 140 is stored in a computer memory for a subsequent trial or iteration and/or further processing for delivery.

At 512, feedback on the interactive interface 126 is updated on the single display. The updated feedback includes the feedback for each dose objective. The updated feedback include the progress of the optimization for the current trial or iteration. For example, the graph 230 is updated with the current trial objective values. Functions of the returned objective values can be computed, such as an average, minimum, maximum, and the like. The functions of the returned objective values can be represented as intermediate composite values, such as a composite target objective value as graphed in reference to FIG. 4.

At 514, the operational status of the RT optimizer unit 102 is determined. If another trial or iteration is to be performed based on the operational status, then processing continues at 504. Processing of acts 510, 512 and 514 can be performed concurrently, simultaneously or in parallel with acts 506 and 508.

At 516, control instructions 152 for the radiation delivery device 106 are generated by the therapy control device 150 based on the optimized plan 140.

At 518, the radiation delivery device 106 delivers radiation according to the control instructions 152.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A radiation therapy system, comprising:
a display device configured display controls on a single display; and
at least one processor and a non-transitory memory for storing instructions that, when executed by the at least one processor, cause the at least one processor to:
receive at least one target structure and at least one organ-at-risk (OAR) structure segmented from a volumetric image;
iteratively generate an optimized RT plan based on at least three dose objectives during a plurality of trials, at least one dose objective of the at least three dose objectives corresponding to each of the at least one target structure and the at least one OAR structure, wherein the optimized RT plan includes a planned radiation dose for each voxel of the volumetric image using external beam radiation therapy;
interactively control each of the at least three dose objectives through the controls displayed on the single display of the display device;
iteratively compute the planned radiation dose according to the controls displayed on the single display of the display device; and
provide visual feedback on the single display according to progress of the at least three dose objectives after each trial, wherein the provided visual feedback includes at least a current composite objective value providing an overall measure of progress in meeting the at least three dose objectives.

2. The system according to claim 1, wherein the controls include controls for one or more parameters of the corresponding dose objective, wherein the one or more parameters include a type of dose, wherein the controls for the one or more parameters for each dose objective are co-located in the single display.

3. The system according to claim 1, wherein the provided visual feedback includes a visual representation of a change in progress of each corresponding dose objective after each trial, wherein the visual representation of the change in progress of each corresponding dose objective is co-located with the corresponding dose objective.

4. The system according to claim 1, wherein the provided visual feedback includes a graphical representation of the progress of the at least three dose objectives over each of the plurality of trials.

5. The system according to claim 1, wherein the controls and the provided visual feedback for the at least three dose objectives are separated into a first region of the single display that includes controls and feedback for each of the at least one OAR structure, and a second region of the single display that includes controls and feedback for each of the at least one target structure.

6. The system according to claim 1, wherein the controls operate concurrently with the at least one processor, wherein changes to any one of the at least three dose objectives are included in a next trial of generating the optimized RT plan based on the at least three dose objectives.

7. The system according to claim 4, wherein the graphical representation of the progress of the at least three dose objectives over each of the plurality of trials includes a line graph of corresponding dose objective values over each of the plurality of trials.

8. The system according to claim 1, wherein the provided visual feedback on the single display further includes at least one of a trend analysis or a labeling of a trial with one or more changed dose objectives.

9. The system according to claim 2, wherein one parameter of each dose objective includes the type of dose, and the type of dose for each dose objective includes one of: a maximum dose volume histogram, a minimum dose volume histogram, a maximum equivalent uniform dose, a minimum equivalent uniform dose, a maximum dose, a minimum dose, a uniform dose objective, a target equivalent uniform dose, or uniformity; wherein each type of dose includes a different visual representation by at least one of a color or a pattern.

10. The system according to claim 1, further including:
a therapy control device configured to receive the optimized RT plan and generate control instructions that control a radiation delivery device to deliver radiation according to the optimized RT plan.

11. A method of radiation therapy, comprising:
interactively controlling each of at least three dose objectives through controls displayed on a single display of a display device, wherein the at least three dose objectives correspond to at least one target structure and at least one organ-at-risk (OAR) structure segmented from a volumetric image, at least one dose objective of the at least three dose objectives corresponds to each of the at least one target structure and the at least one OAR structure;
iteratively computing an optimized RT plan according to the controls, wherein the optimized RT plan includes a planned radiation dose for each voxel of the volumetric image using external beam radiation therapy; and
providing visual feedback on the single display according to progress of the at least three dose objectives after each trial of a plurality of trials, wherein the provided visual feedback includes at least a current composite objective value providing an overall measure of progress in meeting the at least three dose objectives.

12. The method according to claim 11, further comprising:
modifying the at least three dose objectives by at least one of changing one or more parameters of at least one dose objective, or adding a new dose objective.

13. The method according to claim 11, wherein providing visual feedback includes visually representing a change in progress on the single display for each corresponding dose objective after each trial, wherein the visual representation of the change in progress of each corresponding dose objective is co-located with the corresponding dose objective on the single display.

14. The method according to claim 11, wherein providing visual feedback includes graphically representing progress of the at least three dose objectives over each trial of the plurality of trials.

15. The method according to claim 13, wherein the controls and provided visual feedback for the at least three dose objectives are separated into a first region of the single display that includes controls and feedback for each of the at least one OAR structure, and a second region of the single display that includes controls and feedback for each of the at least one target structure.

16. The method according to claim 12, wherein interactively controlling, iteratively computing, and providing feedback are performed concurrently, wherein changes from modifying the at least three dose objectives are included in a next trial of the plurality of trials.

17. The method according to claim 14, wherein graphically representing progress of the at least three dose objectives over each of the plurality of trials includes line graphing of corresponding dose objective values over each of the plurality of trials.

18. The method according to claim 12, wherein changing one or more parameters includes changing a type of dose to one of: a maximum dose volume histogram, a minimum dose volume histogram, a maximum equivalent uniform dose, a minimum equivalent uniform dose, a maximum dose, a minimum dose, a uniform dose objective, a target equivalent uniform dose, or uniformity; wherein each type of dose includes a different visual representation by at least one of a color or a pattern.

19. The method according to claim 11,
generating control instructions for a radiation delivery device to deliver radiation according to the optimized RT plan.

20. A radiation therapy system, comprising:
one or more processors;
a non-transitory storage medium configured with program instructions that when executed by one or more processors, cause the one or more processors to:
interactively control each of at least three dose objectives during a plurality of trials through controls displayed on a single display of a display device, wherein the at least three dose objectives correspond to at least one target structure and at least one organ-at-risk (OAR) structure segmented from a volumetric image, wherein at least one dose objective of the at least three dose objectives corresponds to each of the at least one target structure and the at least one OAR structure;
iteratively compute an optimized RT plan according to the controls, wherein the optimized RT plan includes a planned radiation dose for each voxel of the volumetric image using external beam radiation therapy; and
provide visual feedback on the single display according to progress of the at least three dose objectives after each trial, wherein the provided visual feedback includes at least a current composite objective value providing an overall measure of progress in meeting the at least three dose objectives; and
a therapy control device configured to generate control instructions for a radiation delivery device to deliver radiation according to the optimized RT plan.

* * * * *